United States Patent [19]

Onisi et al.

[11] 4,159,317

[45] Jun. 26, 1979

[54] METHOD FOR PREVENTING ALVEOLAR PYORRHEA

[75] Inventors: Masao Onisi; Keijiro Ishibashi; Soichiro Amao, all of Tokyo, Japan

[73] Assignee: Sankyo Co., Ltd., Tokyo, Japan

[21] Appl. No.: 855,317

[22] Filed: Nov. 28, 1977

Related U.S. Application Data

[63] Continuation of Ser. No. 660,016, Feb. 23, 1976, abandoned, which is a continuation of Ser. No. 574,375, May 5, 1975, abandoned, and a continuation-in-part of Ser. No. 440,295, Feb. 7, 1974, abandoned.

[30] Foreign Application Priority Data

Feb. 26, 1973 [JP] Japan .................................. 48-22842

[51] Int. Cl.² ........................ A61K 7/28; A61K 37/48
[52] U.S. Cl. ......................................... 424/50; 424/94
[58] Field of Search ................................. 424/50, 94

[56] References Cited

FOREIGN PATENT DOCUMENTS 1927411 12/1970 Fed. Rep. of Germany.

OTHER PUBLICATIONS

C.A. 77 #17961(b) (1972); C.A. 75 #106411y (1971); C.A. 70 #65949f (1969); C.A. 68:66564x (1968); C.A. 69 #65384x (1968).
C.A. 79 #77000p (1973); C.A. 78 #151640v (1973); C.A. 78 #157877z (1973); C.A. 76 #44684z (1972).
C.A. 76 #144826r (1972); C.A. 76 #152061c (1972); C.A. 75 #52832r, #52833s, #52834t (1971).
C.A. 75 #101285a (1971); C.A. 74 #130290h, #130291j (1971); C.A. 74 #146415p (1971).

*Primary Examiner*—Shep K. Rose
*Attorney, Agent, or Firm*—Flynn & Frishauf

[57] ABSTRACT

Compositions for the prevention of pyorrhea alveolaris containing a fructan-degrading enzyme at a ratio ranging from 1 to 300 activity units per g. or ml. of the composition.

5 Claims, No Drawings

METHOD FOR PREVENTING ALVEOLAR PYORRHEA

CROSS-REFERENCES TO RELATED APPLICATIONS

This is a continuation, of application Ser. No. 660,016, filed Feb. 23, 1976, now abandoned, which, in turn, is a continuation of Ser. No. 574,375, filed May 5, 1975, abandoned; the last-mentioned application is a continuation-in-part of application Ser. No. 440,295, filed Feb. 7, 1974, now abandoned.

This invention relates to a new use of fructan-degrading enzyme as a preventive agent against periodontal disease.

More particularly, it is concerned with a dental composition for the prevention of periodontal disease which comprises a fructan-degrading enzyme and also with a method for the prevention of periodontal disease which comprises applying a fructan-degrading enzyme to interdental spaces and oral cavity.

It is well-known that periodontal disease is a main manifestation of the so-called paradental disease which frequently causes inflammations in gum and periodontal tissue.

It was disclosed in Sabouraudia, 3, 81 (1963), ibid, 3, 93 (1963) and ibid, 4, 65 (1965) that one of antinomycetes, *Actinomyces viscosus*, is usually isolated from the diseased part of periodontal disease and it was also disclosed in Arch. Oral. Biol., 12, 571 (1967) and J. Dent. Res., 48, (5), 938 (1969) that the microorganism forms a considerable amount of levan, which is a mucous polysaccharide, outside of cell in the presence of sucrose. On the other hand, it was disclosed in Am. J. Pathol., 47, (7), 1157 (1965) that germfree rats monoinfected with *Actinomyces viscosus* exhibit bacterial plaque formation around the molar teeth and pathogenic alterations of the periodontal tissues, including focal bone loss.

In view of the above-depicted facts, we have made further studies on the relationship between the action of *Actinomyces viscosus* and periodontal disease and found that a fructan-degrading enzyme is highly effective as an agent for the prevention of periodontal disease.

It is, accordingly, a primary object of this invention to provide an effective measures for the prevention of periodontal disease.

Other objects and advantages of this invention will be apparent from the following description.

The fructan-degrading enzyme used in a composition according to this invention are produced by, for example, moulds belonging to the genuses Aspergillus, Fusarium, Humicola, Penicillium, Talaromyces, Eupenicillium, Sporotorichum, Chaetomium, Gelasinospora or Stachybotrys, bacteria belonging to the genuses Arthrobacter or Streptococcus and Streptomyces or Actinomyces, as partly disclosed in our copending Japanese Patent Application No. 22843/1973 filed on Feb. 26, 1973. As is obvious to those skilled in the arts, any mutants and variants of the above-described strains are also usable in the present invention. Although all of them can be used, it is better to use a liquefying type (Endo-type) enzyme cutting optionally anywhere the levan molecule than to use a saccharifying type (Exo-type) enzyme cutting and degrading successively from the ends of the levan molecule.

Both a so-called "levanase type" enzyme cutting a straight chain linkage of $\beta$-(2→6) fructan in the levan molecule and a so-called "inulase type" cutting a straight chain linkage of $\beta$-(2→1) fructan in the levan molecule are preferable, but a combination use of more than two fructan-degrading enzyme, each having strong activities is better.

To the compositions according to this invention, other enzymes, for example, such as dextranase, amylase, protease and lipase may be compounded and more effective cleaning activity can be expected by compounding them.

The compositions according to this invention may be formulated by the use of the fructan-degrading enzyme for oral treatment. In order to make the enzyme more effective in interdental spaces and oral cavity, for example, mixing and formulation of the enzyme into toothpaste or powder, troche, gargle and embrocations such as paste, powder or lotion type or mixing them into food, drinks or non-essential edibles such as chewing gums and confectionery may preferably be performed.

An amount of fructan-degrading enzyme contained in these compositions may vary greatly dependant upon the reaction time in oral cavity and the number of uses. The composition may usually contain as a unit dosage about 1 to 3000 activity units per g. or ml. of the composition, preferably about 1 to 300 activity units and most preferably about 10 to 100 activity units, the measurement method of which will be described below. The composition may be usually and preferably applied to patients several times a day and the total daily dosage may be usually of about 1500 activity units. It is naturally preferable for the reaction time to be longer.

The determination of activity is carried out as follows. An enzyme to be determined is added to M/20 citric acid buffered solution (pH 5.4) which contains an amount of 0.5% of fructan (originating from *Aerobacter levanicum*) at 40° C. and reacted for 30 minutes to liberate reducing sugar which is determined as fructose with 3,5-dinitrosalicylic acid. The activity unit for the enzyme is defined as that quantity of the enzyme which liberates 1 mg. of fructose in 60 minutes.

The excellent preventive effect of the present composition will be apparent from the Experiment as given below.

EXPERIMENT

Test on preventive effect of levanase against *Actinomyces viscosus* with gargling Test procedures Nine voluntary subjects under examinations took one drop of caramel and, after 30 minutes, gargled with 5 ml. of a distilled water. Then, the gargling liquid thus vomited was made up to 10 ml. with a distilled water to form a test sample, as a control. Then, the above-mentioned subjects took another drop of caramel and, after 30 minutes, gargled with 5 ml. of an aqueous solution of levanase having a levanase concentration of 100 units/ml. Then, the gargling liquid thus vomited was made up to 10 ml. with a distilled water and the resulting mixture was sufficiently stirred to form a test sample. Assay:

Prevented number of *Actinomyces viscosus* was assayed by spreading the above test sample on a 0.5% propionic acid culture medium in stepwise dilution and cultivating for 48 hours under anaerobic condition.
Results:

The results are summarized in the following Table.

Table

| Subject | Number of *Actinomyces viscosus* | |
|---|---|---|
| | Control (H$_2$O) | Test sample (Levanase) |
| Y | 3.0 × 10$^5$ | 1.03 × 10$^7$ |
| O | 7.44 × 10$^5$ | 2.4 × 10$^6$ |
| To | 7.5 × 10$^4$ | 3.3 × 10$^5$ |
| N | 2.26 × 10$^5$ | 7.8 × 10$^6$ |
| K | 1.54 × 10$^5$ | 5.3 × 10$^5$ |
| O | 1.2 × 10$^5$ | 8.0 × 10$^4$ |
| S | 1.4 × 10$^5$ | 4.5 × 10$^5$ |
| M | 4.0 × 10$^5$ | 4.4 × 10$^5$ |
| Ti | 2.52 × 10$^5$ | 9.52 × 10$^5$ |

It will be apparent from the above results that the difference between the two test samples is significant at the 2% abstention rate by t-test and thus the present composition is highly effective in preventing periodental disease.

The following examples are given to illustrate the present invention, but the activity unit of a fructan-degrading enzyme added, kinds and amounts of carriers and the types of dosage forms can be varied greatly as the case may be and the following examples are not intended to limit the scope of this invention. Further, "%" denotes "weight %" in every example and the activity unit is the same as above described.

EXAMPLE 1

| Toothpaste | |
|---|---|
| Calcium secondary phosphate | 50% |
| Glycerin | 20% |
| Sodium lauryl sulfate | 2.5% |
| Spearmint oil | 2.5% |
| Tragacanth gum | 1.0% |
| Saccharin | 0.1% |
| Water | 23.9% |

To the above composition, the fructan-degrading enzyme originating from *Talaromyces flavus var. flavus* is added in a ratio of 10 activity units/g. of the composition and kneaded to obtain a toothpaste.

EXAMPLE 2

| Liquid-dentifrice | |
|---|---|
| Sodium carboxmethylcellulose | 4.0% |
| Sodium lauryl sulfate | 2.0% |
| Glycerin | 30% |
| Perfume | 0.5% |
| Water | 63.5% |

To the above composition, the fructan-degrading enzyme originating from *Eupenicillium javanicum* is added in a ratio of 10 activity units/g. of the composition and made to dissolve uniformly to obtain liquid dentifrice.

EXAMPLE 3

| Chewing gum | |
|---|---|
| Polyvinyl acetate | 20% |
| Butyl phthalyl butyl glycolate | 3% |
| Polyisobutylene | 3% |
| Microcrystalline wax | 2% |
| Calcium carbonate | 2% |
| Glucose | 69% |
| Perfume | 1% |

To the above composition, the mixture of the fructan-degrading enzymes originating from *Chaetomium subspirale* and *Eupenicillium javanicum* is added in a ratio of 10 activity units/g. of the composition and kneaded to obtain chewing gum.

EXAMPLE 4

| Chewable tablet | |
|---|---|
| Mannitol | 65% |
| Soluble starch | 30% |
| Avicel (manufactured by Asahi Kasei Kogyo K.K., Japan) | 2.5% |
| Pigment for food | trace |
| Aerosil 200 (manufactured by DEGSSA) | 0.6% |
| Magnesium stearate | 0.6% |
| Perfume Saccharin | 0.8% |
| Orange-microne (manufactured by Takasago Perfumery Co., Ltd., Japan) | 0.3% |

To the above composition, the mixture of the fructan-degrading enzymes originating from *Sordaria humana* and *Talaromyces flavus var. flavus* is added in a ratio of 100 activity units/g. of the composition and mixed uniformly and tabulated to give chewable tablets.

EXAMPLE 5

Toothpaste

By the use of the same procedures and formulation as in Example 1 except that the enzyme is added in a ratio of 1 activity unit/g. of the paste instead of the 10 activity units/g., there is obtained a toothpaspte.

EXAMPLE 6

Liquid-dentifrice

By the use of the same procedures and formulation as in Example 2 except that the enzyme is added in a ratio of 1 activity unit/g. of the dentifrice instead of the 10 activity units/g., there is obtained a liquid-dentifrice.

EXAMPLE 7

Chewing gum

By the use of the same procedures and formulation as in Example 3 except that the enzyme is added in a ratio of 1 activity unit/g. of the gum instead of the 10 activity units/g., there is obtained chewing gum.

EXAMPLE 8

Chewable tablet

By the use of the same procedures and formulation as in Example 4 except that the enzyme is added in a ratio of 10 activity units/g. of the tablet instead of the 100 activity units/g., there are obtained chewable tablets.

EXAMPLE 9

| Gargle solution | |
|---|---|
| Glycerol | 50% |
| Perfume | 0.5% |
| Water | 49.5% |

To the above composition, the fructan-degrading enzyme originating from *Talaromyces flavus var. flavus* is added in a ratio of 10 activity units/ml. of the solution to obtain a gargle solution.

Before using, this solution is diluted with water or warm water to 10 times volume.

EXAMPLE 10

Spray for cleaning teeth

The fructan-degrading enzyme as in Example 1 is dissolved in a sterile distilled water at a ratio of 10 activity units/ml. of the solution to obtain a spray solution for dental deterging instruments.

As described in our Japanese Patent Application No. 22843/1973, we have found that a microorganism belonging to the genus Talaromyces, Eupenicillus, Sporotrichum, Sordaria, Chaetomium, Gelasinospora or Stachybotris can produce a fructan-degrading enzyme, which may cut off by hydrolysis $\beta\text{-}2\rightarrow6$ and $\beta\text{-}2\rightarrow1$ fructo-furanoside bond to reduce the viscosity of fructan in a short period of time, and especially a microorganism belonging to the genus Talaromyces has a much higher productivity of a fructan-degrading enzyme than the previously known one does. The process is characterized in that the above-mentioned fructan-degrading enzyme producing microorganism is cultivated and a fructan-degrading enzyme is recovered from a cultured broth.

The above-mentioned fructan-degrading enzyme producing microorganisms have been deposited with the Technical Research Institute of Microbial Industry, Agency of Industrial Science & Technology, Ministry of International Trade and Industry and are available from the Institute of Applied Bacteriology, Tokyo University, and Foundation Fermentation Institute.

| | | Accession No. of |
|---|---|---|
| *Talaromyces flavus vari. flavus* | F 223-B | Application for Deposit and Maintenance of Microorganisms, 1892 |
| *Sordaria humana* | F 651-4 | Microorganisms, 1890 |
| *Chaetomium subspirale* | F 216-4 | Microorganisms, 1888 |
| *Gelasinospora longispora* | F 652-2 | Microorganisms, 1889 |
| *Stachybotris lobulata* | F 61-1 | Microorganisms, 1891 |
| *Eupenicillium javanicum* | F 11-6 | IAM-8067 |
| *Sporotrichum schenkii* | F 61-7 | IFO-5984. |

It should be understood that natural and artificial mutants and variants of the above may be utilized.

The above-listed microorganisms are all known ones and their mycological characteristics are reported as follows:

| | |
|---|---|
| *Talaromyces flavus var. flavus* | Stolk et al; Studies in Micrology, Vol. 2, P. 11 (1972) |
| *Sordaria humana* | Cain: Bibliotheca Mycologica, Vol, 9, p. 18 (1934) |
| *Chaetomium subspirale* | Udagawa: The Journal of General and Applied Microbiolgy, Vol. 6, p. 247 (1960) |
| *Gelasinospora longispora* | Udagawa et al: Transactions of the Mycological Society of Japan, Vol. 8, p. 50 (1954) |
| *Stachybotris lobulata* | Tsubaki: Nagaoa, Vol. 4, p. 16 (1954) |
| *Eupenicillium javanicum* | Stolk et al: Persoonia, Vol. 4, p. 398 (1967) |
| *Sporotrichum schenkii* | Fukumi et al: Byogenbiseibutsugaku-Saikinhen (in Japanese), p. 956 (Igaku-Syoin, 1966). |

In practicing the process, a fructan-degrading enzyme producing microorganism belonging to the genus Talaromyces, Eupenicillium, Sporotrichum, Sordaria, Chaetomium, Gelasinospora or Stachybotris is subjected to surface or submerged culture in a solid or liquid culture medium containing nutrient sources with various compositions commonly employed as natural or artificial media. As nutrient sources may be employed, for example, wheat bran, soybean meal, "Pharmamedia" (manufactured by Traders Oil Mill Company), corn steep liquor, peptone, starch, glucose, sucrose, ammonium sulfate, urea, various inorganic salts or a combination thereof. In particular, when cultivation is done in a culture medium having incorporated therein 0.5-2% of fructan, for example, levan originating from *Aerobacter levanicum* or inulin, 10 or more times increased productivity of a fructan-degrading enzyme can be achieved especially in a liquid culture, as compared with the case of no addition thereof.

It is preferable in cultivation that a temperature is about 28° C. and pH of the culture medium is adjusted to 5.5-7.0. Cultivation time is dependent upon the cultivation condition employed, but cultivation may be discontinued by checking the term to get a maximum activity. Maximum activity may be usually attained by cultivating for 3-5 days.

In order to recover and purify the present enzyme from a liquid cultured broth or a koji extract medium, one may optionally utilize any conventional means previously known for the recovery and purification of an enzyme from a cultured medium containing it. For example, means for concentrating a cultured broth or an aqueous extract of koji under a reduced pressure, salting-out means with ammonium sulfate, sodium sulfate, common salt and the like, fractional precipitation means with such solvent as methanol, ethanol or acetone, adsorption and elution means with a suitable adsorbent, precipitation means with a protein-precipitating agent, isoelectric point precipitation means, separation means of impurities with a heavy metal, electro-dialysis means and the like purification means in combination therewith or alone may be applied.

The fructan-degrading enzyme obtainable by the present process has a strong activity for degradation and rapid liquefaction of fructan. Its optimum active pH is 4-5, optimum temperature is 40°-45° C., stable pH is 3-9 and stable temperature is not higher than 55° C.

Examples are given below.

EXAMPLE 1

Into a 500 ml.-volume Sakaguchi flask were charged 100 ml of a liquid culture medium (pH 6.0) of fructan (originating from *Aerobacter levanicum*) 0.5%, corn steep liquor 0.5%, "Pharmamedia" 0.5%, ammonium sulfate 0.15%, urea 0.05%, acid potassium phosphate 0.2%, magnesium sulfate 0.03%, and calcium chloride 0.03%. The medium was sterilized and inoculated with each of the given fructan-degrading enzyme-producing microorganisms. Shaking culture was effected at 28° C. for 72 hours. Activity of fructan-degrading enzyme was measured according to a viscosity reducing method and a reducing power method. The results are given in the following Table. Methods for measuring its activity are as follows:

Viscosity Reducing Method

To 2 ml. of a 5% solution of fructan (originating from *Aerobacter levanicum*) in M/20 citrate buffer (pH 5.4) was added 0.2 ml. of the cultured broth and the mixture was kept at 40° C. After 3 hours and 19 hours, specific viscosities were measured by means of Ostwald's viscometer.

Reducing Power Method

As representatives of a fructan having a $\beta\text{-}2\rightarrow6$ bond as a main chain bond and of a fructan having a $\beta\text{-}2\rightarrow1$ bond, levan originating from *Aerobacter levanicum* and inulin were selected, respectively. To 1 ml. of a 5% solution of each fructan in M/20 citrate buffer (pH 5.4) was added 1 ml. of the cultured broth. The mixture was left at 40° C. for 30 minutes. Then, a reducing sugar thus formed was measured as fructose according to 3,5-dinitrosalicylic acid method. An amount of the enzyme required to form 1 mg. of fructose in 60 minutes is defined as 1 unit.

| Strain | Reducing power of viscosity | | Reducing power Unit/ml. | |
|---|---|---|---|---|
| | Specific viscosity after 3 hrs. | Specific viscosity after 19 hrs. | Levan substrate | Inulin substrate |
| *Talaromyces flavus vari. flavus* | 1.9 | 0.2 | 18.0 | 14.2 |
| *Sordaria humana* | 3.9 | 1.7 | 0.4 | 0.86 |
| *Chaetomium subspirale* | 4.3 | 2.2 | 2.4 | 9.8 |
| *Gelasinospora longispora* | 4.5 | 2.9 | 0.2 | 8.4 |
| *Stachybotris lobulata* | 5.2 | 3.8 | 0.4 | 0.4 |
| *Eupenicillium javanicum* | 4.1 | 1.3 | 1.6 | 0.2 |
| *Sporotrichum Schenkii* | 2.6 | 1.0 | 3.0 | 9.4 |
| Control | 5.6 | 5.6 | | |

EXAMPLE 2

Into a fermenter with 100 liter volume was charged 50 liters of a liquid culture medium (pH 6.0) prepared by adding to a tap water fructan (originating from *Aerobacter levanicum*) 0.5%, "Pharmamedia" 0.5%, ammonium sulfate 0.15%, urea 0.05%, acid potassium phosphate 0.2%, magnesium sulfate 0.03%. The medium was sterilized and inoculated with 2 liters of a seed culture of *Talaromyces flavus var. flavus* which had previously shaken-cultured at 28° C. for 2 days. Cultivation was effected for 48 hours at 28° C. with 230 r.p.m., aeration of 1 VVm and inner pressure of 1 kg./cm². Activity of fructan-degrading enzyme in the cultured broth (as reducing power unit measured according to Reducing Power Method by the use of a substrate, levan originating from *Aerobacter levanicum*) was 20 units/ml.

The broth was concentrated to 10 liters at a low temperature and to the concentrate was added 3 times volume of acetone to precipitate fructan-degrading enzyme, which was then recovered by filtration and dried under a reduced pressure. 126 g. of an authentic sample of the enzyme were obtained as white powders. Activity of the authentic sample (the same unit as above) was 4375 units/g.

What is claimed is:

1. A method for preventing, alveolar pyorrhea which comprises the steps of applying to gingival placque and periodontal disease causing Actinomyces viscosus inherently present in and insoluble from the interdental spaces and oral cavity of a host infected with said *Actinomyces viscosus*, a fructan-degrading enzyme-containing composition originated from a material selected from the group consisting of moulds belonging to the genuses Aspergillus, Fusarium, Humicola, Penicillium, Talaromyces, Eupenicillium, Sporotorichum, Chaetomium, Gelasinospora and Stachybotrys, bacteria belonging to the genuses Arthrobacter, Streptococcus, Streptomyces and Actinomyces, at a ratio ranging from 1 to 300 activity units per g. or ml. of the composition, said enzyme being in the free state, and thereafter washing out from said interdental spaces and oral cavity Actinomyces viscosus fungus set free therein by enzyme action.

2. The method of claim 1, wherein the material is *Talaromyces flavus var. flavus*.

3. The method of claim 1, wherein the material is *Eupenicillium javanicum*.

4. The method of claim 1, wherein the material is *Chaetomium subspirale*.

5. The method of claim 1, wherein said fructan-degrading enzyme is levanase.

* * * * *